(12) United States Patent
Culver et al.

(10) Patent No.: US 7,053,259 B2
(45) Date of Patent: May 30, 2006

(54) PROCESS OF PRODUCING α-OLEFINS

(75) Inventors: David A. Culver, Salem, NJ (US); Rinaldo S. Schiffino, Wilmington, DE (US); Dewey Lynn Kerbow, Landenburg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 60 days.

(21) Appl. No.: 10/658,233

(22) Filed: Sep. 8, 2003

(65) Prior Publication Data

US 2004/0111002 A1    Jun. 10, 2004

Related U.S. Application Data

(60) Provisional application No. 60/411,449, filed on Sep. 17, 2002.

(51) Int. Cl.
*C07C 2/32* (2006.01)
(52) U.S. Cl. .................. 585/521; 585/511; 585/512; 585/523
(58) Field of Classification Search ............... 585/521, 585/523, 511, 512
See application file for complete search history.

(56) References Cited

U.S. PATENT DOCUMENTS

| | | | |
|---|---|---|---|
| 3,574,782 A * | 4/1971 | Bearden, Jr. et al. ....... | 585/524 |
| 4,020,121 A | 4/1977 | Kister et al. | |
| 6,103,946 A | 8/2000 | Brookhart, III et al. | |
| 2002/0016521 A1 | 2/2002 | Culver et al. | |

OTHER PUBLICATIONS

I. Kroschwitz et al., Kirk-Othmer Encyclopedia of Chemical Technology, 4th Ed., vol. 17, pp. 839-858, John Wiley & Sons, New York.

* cited by examiner

*Primary Examiner*—Thuan D. Dang

(57) ABSTRACT

α-Olefins are made in a modified plug flow reactor system by the oligomerization of ethylene using an iron complex of a selected diimine of a 2,6-pyridinecarboxaldehyde(bisimine) or 2,6-diacylpyridine(bisimine) as the oligomerization catalyst. The reactor is modified to add the iron complex at two or more points along the length of the plug flow reactor, the distance between addition points being dependent on the half-life of the active ethylene oligomerization catalyst.

10 Claims, 2 Drawing Sheets

PROCESS OF PRODUCING α-OLEFINS

Figure 1:
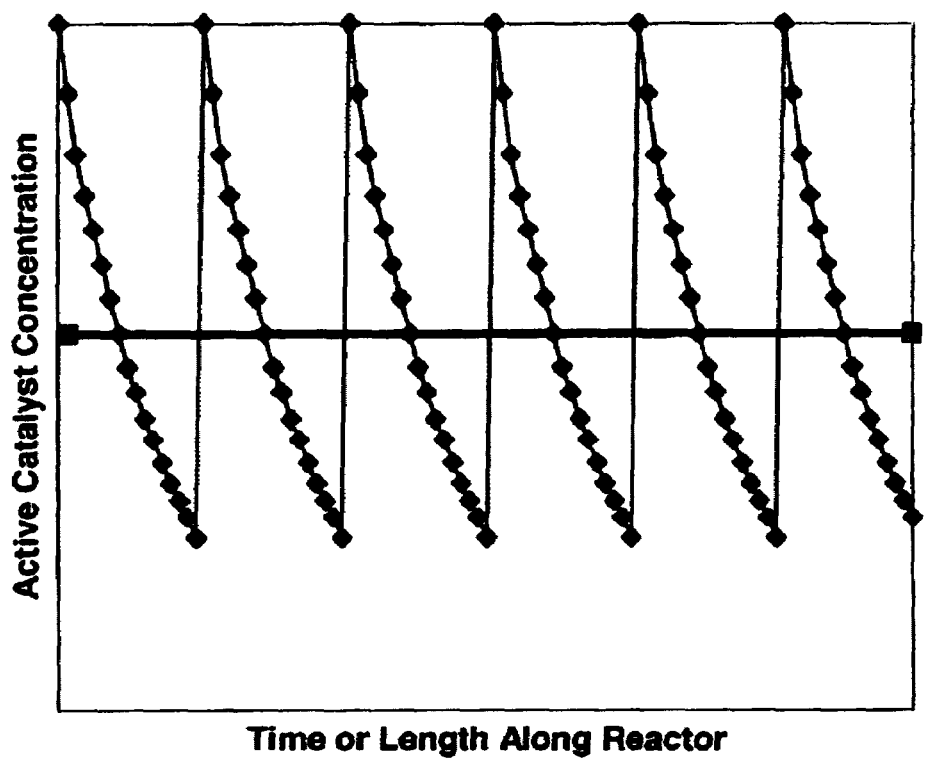

This application claims the benefit of 60/411,449 filed on Sep. 17, 2002.

FIELD OF THE INVENTION

α-Olefins are made in a modified plug flow reactor system by the oligomerization of ethylene using an iron complex of a selected diimine of a 2,6-pyridinecarboxaldehyde or 2,6-diacylpyridine as the oligomerization catalyst.

TECHNICAL BACKGROUND

α-Olefins are important items of commerce, hundreds of millions of kilograms being manufactured yearly. They are useful as monomers for (co)polymerizations and as chemical intermediates for the manufacture of many other materials, for example detergents and surfactants. Presently most α-olefins are made by the catalyzed oligomerization of ethylene by various catalysts, especially certain nickel complexes or aluminum alkyls, see for instance U.S. Pat. No. 4,020,121 and I. Kroschwitz, et al., Ed., *Kirk-Othmer Encyclopedia of Chemical Technology*, 4$^{th}$ Ed., Vol. 17, John Wiley & Sons, New York, pp. 839–858. Depending on the catalyst used and the product distribution desired various processes are used, but they tend to operate at high pressures, and/or high temperatures, and/or have large recycle streams, and/or be complex (for example recycle of catalyst streams), all of which increases the capital cost of the manufacturing plant and/or increases plant operating costs, both of course undesirable. Therefore, better processes for making α-olefins are of commercial interest. Some of the processes which use these catalysts, especially alkylaluminum compound (alone) catalysts, are reported to utilize plug flow reactors.

Recently, as reported in U.S. Pat. No. 6,103,946, which is hereby incorporated by reference, it has been found that iron complexes of certain tridentate ligands of 2,6-pyridinecarboxaldehye(bisimines) or 2,6-diacylpyridine(bisimines) are excellent catalysts for the production of α-olefins from ethylene. U.S. Patent Application Publication 2002/0016521 describes a manufacturing process for α-olefins using these catalysts in which a liquid full continuous stirred tank reactor is used, optionally followed by a final reactor which may be plug flow reactor. The process described herein concerns a modified plug flow reactor.

SUMMARY OF THE INVENTION

This invention concerns, a process for the preparation of α-olefins, comprising, contacting at about 40° C. to about 150° C. in a liquid full modified plug flow reactor:
(a) an oligomerization catalyst which is an iron complex of a 2,6-pyridinecarboxaldehye(bisimine) or a 2,6-diacylpyridine(bisimine) which oligomerizes ethylene to α-olefins;
(b) ethylene;
(c) an organic solvent; and
(d) optionally one or more cocatalysts;
wherein (a) plus (b) plus (c) plus (d), when present, form a process mixture, and wherein along the length of said modified plug flow reactor said oligomerization catalyst is added at two or more addition points to said process mixture, so that a time interval for said process mixture between said addition points is about 0.3 to about 5 half lives of said oligomerization catalyst under process conditions.

DETAILS OF THE INVENTION

Herein, certain terms are used. Some of them are:

A "hydrocarbyl group" is a univalent group containing only carbon and hydrogen. As examples of hydrocarbyls may be mentioned unsubstituted alkyls, cycloalkyls and aryls. If not otherwise stated, it is preferred that hydrocarbyl groups (and alkyl groups) herein contain 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the oligomerization process or operation of the oligomerization catalyst system. If not otherwise stated, it is preferred that substituted hydrocarbyl groups herein contain 1 to about 30 carbon atoms. Included in the meaning of "substituted" are rings containing one or more heteroatoms, such as nitrogen, oxygen and/or sulfur, and the free valence of the substituted hydrocarbyl may be to the heteroatom. In a substituted hydrocarbyl, all of the hydrogen may be substituted, as in trifluoromethyl.

By "(inert) functional group" herein is meant a group, other than hydrocarbyl or substituted hydrocarbyl, which is inert under the process conditions to which the compound containing the group is subjected. The functional groups also do not substantially deleteriously interfere with any process described herein that the compound in which they are present may take part in. Examples of functional groups include halo (fluoro, chloro, bromo and iodo), and ether such as —OR$^{50}$ wherein R$^{50}$ is hydrocarbyl or substituted hydrocarbyl. In cases in which the functional group may be near a transition metal atom, the functional group alone should not coordinate to the metal atom more strongly than the groups in those compounds that are shown as coordinating to the metal atom, that is they should not displace the desired coordinating group.

By a "cocatalyst" or a "catalyst activator" is meant one or more compounds that react with a transition metal compound to form an activated catalyst species. One such catalyst activator is an "alkyl aluminum compound" which, herein, means a compound in which at least one alkyl group is bound to an aluminum atom. Other groups such as, for example, alkoxide, hydride, an oxygen atom bridging two aluminum atoms, and halogen may also be bound to aluminum atoms in the compound.

By a "linear α-olefin product" is meant a composition predominantly comprising a compound or mixture of compounds of the formula $H(CH_2CH_2)_qCH=CH_2$ wherein q is an integer of 1 to about 18. In most cases, the linear α-olefin product of the present process will be a mixture of compounds having differing values of q of from 1 to 18, with a minor amount of compounds having q values of more than 18. Preferably, less than 50 weight percent, and more preferably less than 20 weight percent, of the product will have q values over 18. The product may further contain small amounts (preferably less than 30 weight percent, more preferably less than 10 weight percent, and especially preferably less than 2 weight percent) of other types of compounds such as alkanes, branched alkenes, dienes and/or internal olefins.

By a "primary carbon group" herein is meant a group of the formula —CH$_2$—, wherein the free valence—is to any other atom, and the bond represented by the solid line is to a ring atom of a substituted aryl to which the primary carbon group is attached. Thus the free valence—may be bonded to a hydrogen atom, a halogen atom, a carbon atom, an oxygen atom, a sulfur atom, etc. In other words, the free valence—may be to hydrogen, hydrocarbyl, substituted hydrocarbyl or a functional group. Examples of primary carbon groups include —$CH_3$, —$CH_2CH(CH_3)_2$, —$CH_2Cl$, —$CH_2C_6H_5$, —$OCH_3$ and —$CH_2OCH_3$.

By a "secondary carbon group" is meant the group

wherein the bond represented by the solid line is to a ring atom of a substituted aryl to which the secondary carbon group is attached, and both free bonds represented by the dashed lines are to an atom or atoms other than hydrogen. These atoms or groups may be the same or different. In other words the free valences represented by the dashed lines may be hydrocarbyl, substituted hydrocarbyl or inert functional groups. Examples of secondary carbon groups include —CH($CH_3$)$_2$, —$CHCl_2$, —CH($C_6H_5$)$_2$, cyclohexyl, —CH($CH_3$)$OCH_3$, and —CH=$CCH_3$.

By a "tertiary carbon group" is meant a group of the formula

wherein the bond represented by the solid line is to a ring atom of a substituted aryl to which the tertiary carbon group is attached, and the three free bonds represented by the dashed lines are to an atom or atoms other than hydrogen. In other words, the bonds represented by the dashed lines are to hydrocarbyl, substituted hydrocarbyl or inert functional groups. Examples of tetiary carbon groups include —C($CH_3$)$_3$, —C($C_6H_5$)$_3$, —$CCl_3$, —$CF_3$, —C($CH_3$)$_2OCH_3$, —C≡CH, —C($CH_3$)$_2$CH=$CH_2$, aryl and substituted aryl such as phenyl and 1-adamantyl.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By a "first ring atom in $R^6$ and $R^7$ bound to an imino nitrogen atom" is meant the ring atom in these groups bound to an imino nitrogen shown in (I), for example

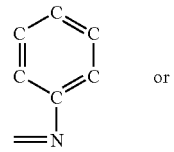

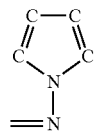

the atoms shown in the 1-position in the rings in (II) and (III) are the first ring atoms bound to an imino carbon atom (other groups which may be substituted on the aryl groups are not shown). Ring atoms adjacent to the first ring atoms are shown, for example, in (IV) and (V), where the open valencies to these adjacent atoms are shown by dashed lines [the 2,6-positions in (IV) and the 2,5-positions in (V)].

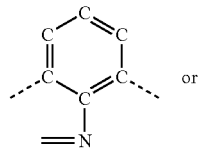

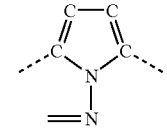

By "liquid full" herein is meant that at least about 85 volume percent, preferably at least about 95 volume percent, of the reactor volume is occupied by a liquid that is a single phase. Small amounts of the reactor volume may be taken up by gas, for example ethylene may be added to the reactor as a gas, which is absorbed by the liquid phase rapidly under the process conditions. Nevertheless, some small amount of dissolving ethylene gas may be present. Not counted in the reactor volume is any solid resulting from fouling of the reactor (walls).

By a "bubble point" herein is meant the minimum pressure that must be exerted on the process ingredients to keep all of the ingredients, including ethylene, in the process in the liquid phase (i.e., dissolved). The bubble point pressure will vary with the temperature of the process and the composition of the liquid phase. For example, as the temperature is raised, the minimum pressure needed to maintain a liquid phase (including ethylene) without an ethylene gas phase will increase, and vice versa. The bubble point pressure also changes with the composition of the liquid medium. The bubble point may be measured under various conditions using a pressure cell with a viewport to determine the minimum pressure which, under a given set of conditions, the ethylene gas phase "disappears". Specific techniques that are useful for measuring bubble points will be found in A. Y. Dandekar, et al., *Ind. Eng. Chem. Res.*, vol. 39, p. 2586–2591 (2000); WO 98/45691; and S. Raham, et al., *J. Pet. Sci. Eng.*, vol. 14, p. 25–34 (1995), all of which are hereby incorporated by reference.

Herein a modified plug flow reactor (sometimes called a tubular reactor) is used. Plug flow reactors are well known in the art, see for instance J. I. Kroschwitz, et al., Ed., *Kirk-Othmer Encyclopedia of Chemical Technology*, 4th Ed., Vol. 20, John Wiley & Sons, New York, 1996, p. 1007–1059, which is incorporated by reference herein. The plug flow reactor herein is typically a long tube or pipe having an inside diameter of about 3 cm to 15 cm, the tube being thick enough to withstand the pressure of the reaction mixture. At the feed end (where ingredients enter) of the reactor solvent (some or all of the solvent may be α-olefins which are produced in the process), ethylene, the iron complex and optionally cocatalyst are added and pumped through the reactor at a given rate. The iron complex and/or cocatalyst (if present) may be added as a suspension (the iron complex and/or cocatalyst being solids) in a liquid. "Liquid full" herein includes when small the catalyst and/or cocatalyst are solids (as slurries) in the liquid phase. The catalyst and/or cocatalyst may also be added as part of a supported particulate catalyst, i.e., they are supported on a support. During the trip through the length of the reactor, the ethylene is converted to a mixture of α-olefins. The liquid in the reactor proceeds through the tube at approximately a constant linear rate, unless substantial amounts (compared to the total ingredients fed to the feed end) of materials, such as ethylene are fed along the length of the reactor. If such amounts are fed to the reactor, the linear velocity of the process ingredients through the reactor will increase. As the liquid proceeds through the reactor, the catalytic activity of the iron catalyst typically decays with time. In order to maintain the catalytic activity of the iron catalyst, the plug flow reactor system is "modified" by having addition points for the iron complex along the length of the reactor. These addition points are spaced along the length of the reactor so that the time interval between addition points for the process mixture between addition points is about 0.3 to about 5 half lives, preferably about 0.5 to about 3.0 half lives, and more preferably about 0.8 to about 2.0 half lives, of the catalytic activity of the iron complex. Any of the above minimum half-life intervals may be combined with any maximum half-life interval. Thus, the distance between these addition points will depend on the half-life of the iron complex under the process conditions being used, as well as the velocity of the process mixture through the plug flow reactor. The faster the velocity of the process mixture and/or the longer the half-life of the iron complex the further the linear distance between addition points.

The iron complex used herein is an iron complex of a 2,6-pyridinecarboxaldehye(bisimine) or a 2,6-diacylpyridine(bisimine). A preferred ligand in the iron complex has the formula

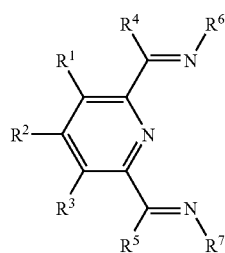

(I)

wherein:

$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

In one preferred compound (I) $R^6$ is

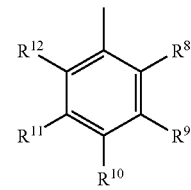

(VI)

and $R^7$ is

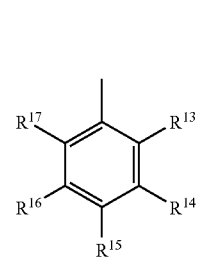

(VII)

wherein:

$R^8$ is a halogen, a primary carbon group, a secondary carbon group or a tertiary carbon group; and $R^9$, $R^{10}$, $R^{11}$, $R^{14}$, $R^{15}$, $R^{16}$ and $R^{17}$ are each independently hydrogen, hydrocarbyl, substituted hydrocarbyl or a functional group; provided that:

when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or when $R^8$ is a tertiary carbon group, none or one of $R^{12}$, $R^{13}$ and $R^{17}$ is tertiary carbon group, with the remainder of $R^{12}$, $R^{13}$ and $R^{17}$ being hydrogen;

and further provided that any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

In the above formulas (VI) and (VII), $R^8$ corresponds to the second ring atom adjacent to the first ring atom bound to the imino nitrogen, and $R^{12}$, $R^{13}$ and $R^{17}$ correspond to the other ring atoms adjacent to the first ring atom.

In compounds (I) containing (VI) and (VII), it is particularly preferred that:

if $R^8$ is a primary carbon group, $R^{13}$ is a primary carbon group, and $R^{12}$ and $R^{17}$ are hydrogen; or if $R^8$ is a secondary carbon group, $R^{13}$ is a primary carbon group or a secondary carbon group, more preferably a secondary carbon group, and $R^{12}$ and $R^{17}$ are hydrogen; or if $R^8$ is a tertiary carbon group (more preferably a trihalo tertiary carbon group such as a trihalomethyl), $R^{13}$ is a tertiary carbon group (more preferably a trihalotertiary group such as a trihalomethyl), and $R^{12}$ and $R^{17}$ are hydrogen, or if $R^8$ is a halogen, $R^{13}$ is a halogen, and $R^{12}$ and $R^{17}$ are hydrogen.

In all specific preferred compounds (I) in which (VI) and (VII) appear, it is preferred that $R^1$, $R^2$ and $R^3$ are hydrogen; and/or $R^4$ and $R^5$ are methyl. It is further preferred that:

$R^9$, $R^{10}$, $R^{11}$, $R^{12}$, $R^{14}$, $R^{15}$, $R^{16}$ and $R^{17}$ are all hydrogen; $R^{13}$ is methyl; and $R^8$ is a primary carbon group, more preferably methyl; or $R^9$, $R^{10}$, $R^{11}$, $R^{12}$, $R^{14}$, $R^{15}$, $R^{16}$ and $R^{17}$ are all hydrogen; $R^{13}$ is ethyl; and $R^8$ is a primary carbon group, more preferably ethyl; or $R^9$, $R^{10}$, $R^{11}$, $R^{12}$, $R^{14}$, $R^{15}$, $R^{16}$ and $R^{17}$ are all hydrogen; $R^{13}$ is isopropyl; and $R^8$ is a primary carbon group, more preferably isopropyl; or $R^9$, $R^{10}$, $R^{11}$, $R^{12}$, $R^{14}$, $R^{15}$, $R^{16}$ and $R^{17}$ are all hydrogen; $R^{13}$ is n-propyl; and $R^8$ is a primary carbon group, more preferably n-propyl; or $R^9$, $R^{10}$, $R^{11}$, $R^{12}$, $R^{14}$, $R^{15}$, $R^{16}$ and $R^{17}$ are all hydrogen; $R^{13}$ is chloro; and $R^8$ is a halogen, more preferably chloro; or $R^9$, $R^{10}$, $R^{11}$, $R^{12}$, $R^{14}$, $R^{15}$, $R^{16}$ and $R^{17}$ are all hydrogen; $R^{13}$ is trihalomethyl, more preferably trifluoromethyl; and $R^8$ is a trihalomethyl, more preferably trifluoromethyl.

In another preferred embodiment of (I), $R^6$ and $R^7$ are, respectively

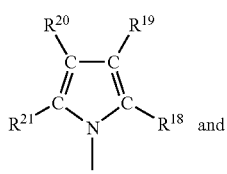

(VIII)

and

-continued

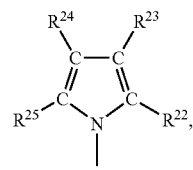

(IX)

wherein:

$R^{18}$ is a halogen, a primary carbon group, a secondary carbon group or a tertiary carbon group; and $R^{19}$, $R^{20}$, $R^{23}$ and $R^{24}$ are each independently hydrogen, hydrocarbyl, substituted hydrocarbyl or a functional group;

Provided that:

when $R^{18}$ is a halogen or primary carbon group none, one or two of $R^{21}$, $R^{22}$ and $R^{25}$ are a halogen or a primary carbon group, with the remainder of $R^{21}$, $R^{22}$ and $R^{25}$ being hydrogen; or when $R^{18}$ is a secondary carbon group, none or one of $R^{21}$, $R^{22}$ and $R^{25}$ is a halogen, a primary carbon group or a secondary carbon group, with the remainder of $R^{21}$, $R^{22}$ and $R^{25}$ being hydrogen;

when $R^{18}$ is a tertiary carbon group, none or one of $R^{21}$, $R^{22}$ and $R^{25}$ is a tertiary carbon group, with the remainder of $R^{21}$, $R^{22}$ and $R^{25}$ being hydrogen;

and further provided that any two of $R^{18}$, $R^{19}$, $R^{20}$, $R^{21}$, $R^{22}$, $R^{23}$, $R^{24}$ and $R^{25}$ vicinal to one another, taken together may form a ring.

In the above formulas (VII) and (IX), $R^{18}$ corresponds to the second ring atom adjacent to the first ring atom bound to the imino nitrogen, and $R^{21}$, $R^{22}$ and $R^{25}$ correspond to the other ring atoms adjacent to the first ring atom.

In compounds (I) containing (VII) and (IX), it is particularly preferred that:

if $R^{18}$ is a primary carbon group, $R^{22}$ is a primary carbon group, and $R^{21}$ and $R^{25}$ are hydrogen; or if $R^{18}$ is a secondary carbon group, $R^{22}$ is a primary carbon group or a secondary carbon group, more preferably a secondary carbon group, and $R^{21}$ and $R^{25}$ are hydrogen; or if $R^{18}$ is a tertiary carbon group (more preferably a trihalo tertiary carbon group such as a trihalomethyl), $R^{22}$ is a tertiary carbon group (more preferably a trihalotertiary group such as a trihalomethyl), and $R^{21}$ and $R^{25}$ are hydrogen; or if $R^{18}$ is a halogen, $R^{22}$ is a halogen, and $R^{21}$ and $R^{25}$ are hydrogen.

In all specific preferred compounds (I) in which (VII) and (IX) appear, it is preferred that $R^1$, $R^2$ and $R^3$ are hydrogen; and/or $R^4$ and $R^5$ are methyl. It is further preferred that:

$R^{19}$, $R^{20}$, $R^{21}$, $R^{23}$ and $R^{24}$ are all hydrogen; $R^{22}$ is methyl; and $R^{18}$ is a primary carbon group, more preferably methyl; or $R^{19}$, $R^{20}$, $R^{21}$, $R^{23}$ and $R^{24}$ are all hydrogen; $R^{22}$ is ethyl; and $R^{18}$ is a primary carbon group, more preferably ethyl; or $R^{19}$, $R^{20}$, $R^{21}$, $R^{23}$ and $R^{24}$ are all hydrogen; $R^{22}$ is isopropyl; and $R^{18}$ is a primary carbon group, more preferably isopropyl; or $R^{19}$, $R^{20}$, $R^{21}$, $R^{23}$ and $R^{24}$ are all hydrogen; $R^{22}$ is n-propyl; and $R^{18}$ is a primary carbon group, more preferably n-propyl; or $R^{19}$, $R^{20}$, $R^{21}$, $R^{23}$ and $R^{24}$ are all hydrogen; $R^{22}$ is chloro or bromo; and $R^{18}$ is a halogen, more preferably chloro or bromo.

Compound (I) and its iron complexes (the oligomerization catalyst) may be prepared by a variety of methods, see for instance previously incorporated U.S. Pat. No. 5,955,555 and WO 99/02472, as well as WO 99/50273 (equivalent to U.S. patent application Ser. No. 09/277,910, filed Mar. 29, 1999) and WO 00/08034, all of which are also included by reference.

The use of 2,6-pyridinecarboxaldehyde(bisimine) or 2,6-diacylpyridine(bisimine) as ethylene oligomerization and/or polymerization catalysts, and the general conditions for such reactions, including temperature, pressure, supportation of the iron complex (if desired), useful cocatalysts and amounts, much of which is useful herein, may be found in U.S. Pat. Nos. 5,955,555, 6,103,946, World Patent Applications 02/06192, 02/12151, and U.S. Provisional Patent Application 60/285,554, filed Apr. 20, 2001 (CL1844 PRV1), all of which are hereby included by reference. A preferred temperature range for the process (ingredients within the reactor) is about 50° C. to about 120° C., preferably about 70° C. to about 110° C. Another preferred temperature range because maximum catalyst efficiency is achieved is about 40° C. to about 70° C., but this may be difficult to achieve because of the potential cost of maintaining such low temperatures (cooling). It is to be understood that over the length of the reactor there may be small portions in which the process mixture is outside this temperature range, but over the majority of the length of the reactor, the process ingredients are within this range.

By the "half life of the iron complex" or the "half life of the activity of the iron complex" is meant the amount of time during which the iron complex loses one half of its activity towards oligomerizing ethylene. The concept of half lives is well known in the art of chemical kinetics, see for instance A. A. Frost, et al., Kinetics and Mechanism, $2^{nd}$ Ed., John Wiley & Sons, New York, 1961 (especially chapter 3), which is hereby included by reference. These can be determined from kinetic measurements in commercial plant size plug flow reaction system under conditions that will be actually used in the manufacturing process. More typically it will be determined in a model (laboratory) reaction system which mimics the conditions in a commercial manufacturing plant. Alternatively the half life may be at least approximately determined by use of a batch or semibatch (ethylene being fed during the oligomerization) reactor by using oligomerization conditions similar to those to be used in the desired modified plug flow reactor. For instance the fall in (mostly ethylene) pressure in a batch reactor, or the uptake of ethylene in a may be used as a measure of the oligomerization catalyst activity with time. As is well understood in the art, suitable calibrations for ethylene concentration vs. total pressure in the batch reactor, and apparent ethylene uptake vs. actual ethylene uptake in a semibatch reactor should be made.

It is believed the main influence on the half life of these iron complexes is the temperature of the reaction, assuming substantial amounts deleterious impurities are not allowed into the reaction system, and that ethylene is present in substantial excess. Other factors such as solvent type, ethylene pressure, concentrations of various ingredients, type of cocatalyst, etc., are believed to have at best only a minor contribution to the half-life of these catalysts. Table A below gives the approximate half-lives of (X) and (XI) at various temperatures.

TABLE A

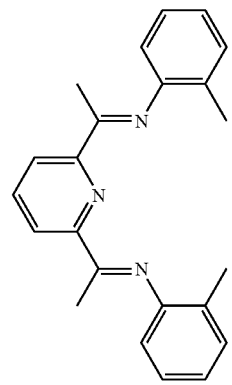

(X)

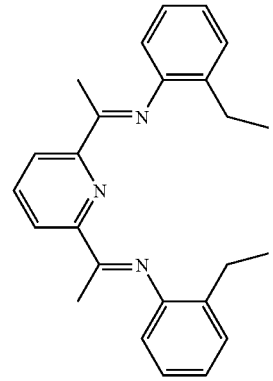

(XI)

| Temp, ° C. | Half-life, min | |
| --- | --- | --- |
| | (X) | (XI) |
| 40 | 26 | 9 |
| 60 | 11 | 2 |
| 80 | 6 | 1 |
| 100 | 3 | — |

These half-lives were determined in a semibatch reactor with a toluene solvent, in which ethylene was added to the reactor at a constant pressure. The uptake of ethylene was measured with time and used (with appropriate corrections) to calculate the rate constant (and hence half-lives) for decay of the catalyst activity.

The modified plug flow reactor will typically be a long tube or pipe along which the process ingredients flow. The "beginning" end wherein the process ingredients are first fed is called the "feed end" herein, and the end where the process ingredients exit the reactor is called the "exit" herein. Since the oligomerization is exothermic and the temperature is usually controlled to some maximum (range), cooling is usually provided to the reactor. Typically the reactor will be immersed in some type of cooling liquid. For example this may be a cooled water or brine solution, or may be a liquid which vaporizes (at the pressure the liquid is under) to cool the liquid. The vapor is typically cooled and condensed back to liquid and returned to the cooling liquid. A useful configuration for the reactor and its associated cooling equipment is a so-called shell and tube configuration, in which the reactor (except for the ends of the reactor) is inside a shell. The reactor (tube), which is usually coiled, is surrounded by the liquid cooling medium, which is inside the shell.

It is preferred that the oligomerization is run in an inert solvent such as a hydrocarbon. Useful hydrocarbons include alkanes such as heptane, or nonane, or aromatic hydrocarbons such as toluene or xylene. Preferably the solvent has a boiling point that allows it be readily separated by distillation from the α-olefins produced in the process. At the feed end, the iron complex, usually a cocatalyst, solvent and ethylene are added to the reactor (perhaps through a mixing tee or other mixing apparatus), and these materials start traveling down the plug flow reactor towards the exit. As the oligomerization proceeds the process mixture is typically heated by the exothermic reaction, while being cooled by the cooling liquid outside the reactor. Because the oligomerization catalyst activity decays with time, especially at elevated temperatures, the concentration of active oligomerization catalyst decreases as the process mixture travels through the reactor. Therefore the absolute rate of α-olefin synthesis will slow and the process mixture will cool. The amount of ethylene present will also decrease as it reacts to form α-olefins (see below). Therefore at some point along the reactor, more oligomerization catalyst (iron complex) and optionally also more cocatalyst, will be injected into the reactor, and hence process stream. This is about 0.5 to about 5.0 iron complex half-lives from the feed end. Since there is already some active oligomerization catalyst remaining in the process stream the amount injected (iron complex and/or cocatalyst) may be less than was injected at the feed end. The cocatalyst may be injected at the same point as the iron complex, or at different points along the reactor, but it is preferred that it be injected at the same point. This may be repeated numerous times as the process stream flows through the reactor, but preferably the number of injection points (including the addition at the feed end) is typically about 2 to about 10, more preferably about 3 to about 8. This will be determined somewhat by the half-life time, the flow rate through the reactor, and the length of the reactor. The concentration of the active oligomerization complex through the reactor can be empirically represented as shown in FIG. 1, where the y axis is oligomerization catalyst concentration and the x axis is time of the reaction mixture from the feed end or position along the reactor from the feed end.

As mentioned above ethylene fed to the reactor at the feed end is also "used up" during the reaction. It may be possible to add enough ethylene to the process mixture at the feed end so that no more additions are necessary, but this may result in one or more disadvantages while running the process. The very high concentration of ethylene near the feed end may cause an excessive amount of heat to be generated near the feed end, causing excessive temperature of the process mixture, and/or the concentration of ethylene may decrease greatly over the length of the reactor complicating efforts to have relatively similar amounts of reaction along the length of the reactor, and/or it may not be possible to remove as much ethylene as desired from the reaction mixture (see below) towards the exit of the reactor. Therefore one may optionally also add ethylene at various (second addition) points along the reactor length, so as to maintain the ethylene concentration relatively steady over the length of the reactor, except perhaps near the exit. It is often convenient to add the ethylene at the same points along the reactor where the oligomerization catalyst is injected, although that is not necessary. The fewer total (ethylene, oligomerization catalyst, etc) injection points there are, the cheaper the reactor may be to build and/or operate. The ethylene concentration in a reactor with multiple injection points is generically shown in FIG. 2, where the y axis is ethylene concentration, and the x axis is time of the reaction mixture from the feed end or position along the reactor from the feed end.

Figure 2:
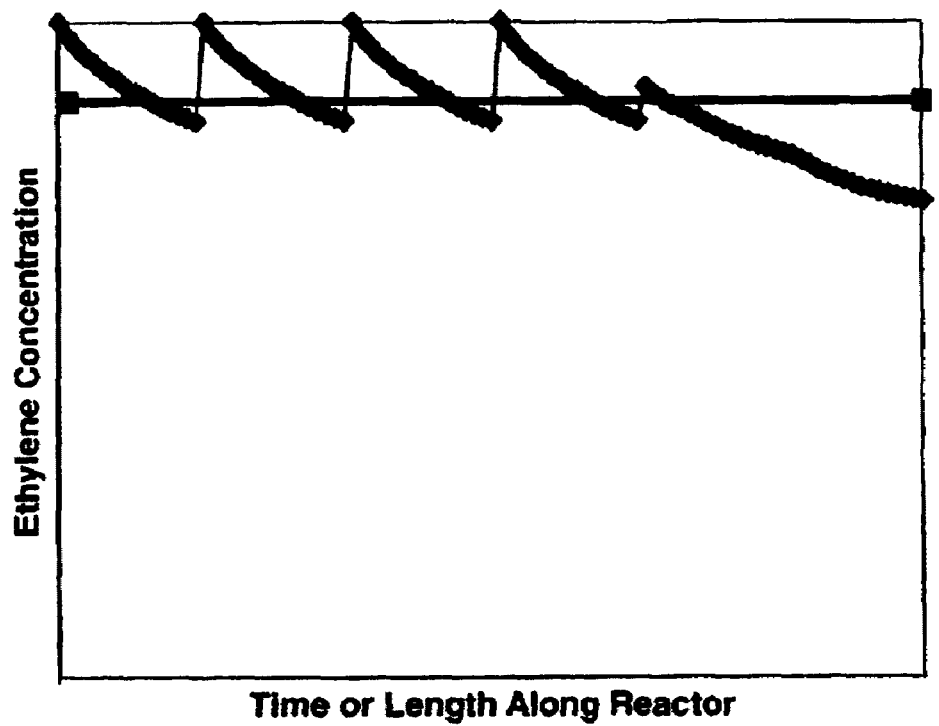

Towards the exit of the reactor it may be desirable to reduce the ethylene concentration greatly to reduce the amount of ethylene that is recycled back to the feed end of the reactor. This often results in lower equipment and operating costs for the recycling of this ethylene, and so is often desirable. This is depicted in FIG. 2, which shows no ethylene injection towards the exit of the reactor.

As an illustration the following can be envisioned. One has a tubular reactor, 0.03 m inside diameter and 4500 m long, having 3 injection points, of which can handle one or more of iron complex, ethylene (injected at 13.8 MPa pressure) and cocatalyst, one point at the feed end, a second point 1500 m downstream, and a third point 1500 m downstream of the second injection point. The reactor is cooled with liquid pentane held at a temperature of 70° C. Cooling is accomplished by allowing the pentane to vaporize. The pentane vapor is condensed and returned to the pentane liquid coolant. The iron complex, (X), contains 11.9 wt % Fe (as metal), and this is the weight shown in Table B. The iron complex is fed as a slurry in a small amount of a suspending medium such as mineral oil. The cocatalyst is methylaluminoxane in o-xylene containing 7-wt % Al (as metal). In order to accommodate the need to maintain the temperature at 70–80° C. (it increases to about 80° C. after each catalyst injection, and then decreases to about 70° C. until the next injection point) one can calculate the feed data in Table B.

TABLE B

| | Feeds | | |
|---|---|---|---|
| | Injection #1 | Injection #2 | Injection #3 |
| ethylene (kg/h) | 500 | 368 | 180 |
| catalyst (g/h) | 0.77 | 0.92 | 1.11 |
| cocatalyst (g/h) | 193 | 229 | 278 |
| solvent (kg/h) | 900 | 0 | 0 |

The total holdup time in the reactor is about 64 minutes, and the time between injection points 1 and 2 is 27.5 min, and between points 2 and 3 is about 18.5 minutes. These vary because of the introduction of additional ethylene at feed points 2 and 3. Assuming the average temperature in the reactor is 75° C., this means the number of half lives of the active polymerization catalyst between injection points 1 and 2 is 3.9, and between injection points 2 and 3 is 2.6. Under these conditions it is believed about 80 percent, or about 838 kg, of the ethylene fed to the reactor will be oligomerized. The increased amount of catalyst which can be fed is due to the increase in mass of the fluid going through the reactor because of the additional ethylene feeds, which can absorb more heat for a given temperature differential.

Compared to a continuous stirred tank reactor (CSTR) the modified plug flow reactor has several advantages. Probably the most important of these is higher α-olefin product purity. In a CSTR the concentration of α-olefin is constant and relatively high during the oligomerization reaction. It is believed that most of the impurities found in the α-olefin product arise from reaction of already formed α-olefins with "new" oligomer chains (made from ethylene) attached to the active oligomerization complex, and/or by reaction of the iron complex with already formed α-olefins. In either event, the lower the concentration of α-olefins in the process mixture, the less impurities will be formed. In the modified plug flow reactor the average concentration of α-olefins along the length of the reactor is much lower than the concentration in a CSTR, since the concentration of α-olefins builds up along the length of the reactor to the final concentration exiting the reactor. For example, at the feed end the concentration of α-olefins is zero.

Also in the modified plug flow reactor, the concentration of oligomerization catalyst is on the average lower than in a CSTR, thereby also resulting (especially when the α-olefin content is high) in a lesser production of impurities in the α-olefins produced. When ethylene concentration is low, impurities may also be more readily produced. The modified plug flow reactor may be designed so that when the ethylene concentration is relatively low the active oligomerization catalyst concentration is also relatively low (see FIGS. 1 and 2). All of these factors contribute to purer α-olefins often being produced by the modified plug flow reactor process than in a CSTR process. Alternatively the modified plug flow process may produce a process stream which contains a higher concentration of α-olefins at the same purity produced by a CSTR process, or any combination of these two factors α-olefin concentration and purity).

Finally in the modified plug flow reactor in order to produce the same concentration of α-olefins in the final product stream, compared to an unmodified plug flow reactor, lower ethylene pressures may be used. This may result in lower capital costs for the modified plug flow reactor and its associated piping, and/or lower capital and/or operating costs for compressing recycle and/or makeup ethylene in the reactor system.

What is claimed is:

1. A process for the preparation of α-olefins, comprising, contacting at about 40° C. to about 120° C. in a liquid full modified plug flow reactor:
   (a) an oligomerization catalyst which is an iron complex of a 2,6-pyridinecarboxaldehyde(bisimine) or a 2,6-diacylpyridine(bisimine) which oligomerizes ethylene to α-olefins;
   (b) ethylene;
   (c) an organic solvent; and
   (d) optionally one or more cocatalysts;
wherein (a) plus (b) plus (c) plus (d), when present, form a process mixture, and wherein along the length of said modified plug flow reactor said oligomerization catalyst is added at two or more first addition points to said process mixture, so that a time interval for said process mixture between said addition points is about 0.3 to about 5 half lives of said oligomerization catalyst under process conditions.

2. The process as recited in claim 1 wherein said time interval is about 0.5 to about 3.0 of said half lives.

3. The process as recited in claim 1 wherein said 2,6-pyridinecarboxaldehyde(bisimine) or 2,6-diacylpyridine(bisimine) is

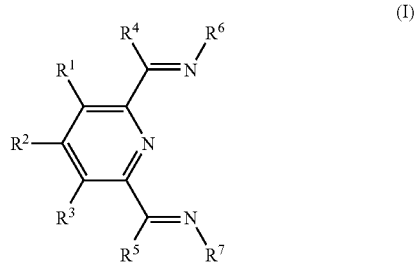

(I)

wherein:
$R^1$, $R^2$ and $R^3$ are each independently hydrogen, hydrocarbyl, substituted hydrocarbyl or an inert functional group, provided that any two of $R^1$, $R^2$ and $R^3$ vicinal to one another taken together may form a ring;

$R^4$ and $R^5$ are each independently hydrogen, hydrocarbyl, substituted hydrocarbyl or an inert functional group;

$R^6$ and $R^7$ are each independently a substituted aryl having a first ring atom bound to the imino nitrogen, provided that:

in $R^6$, a second ring atom adjacent to said first ring atom is bound to a halogen, a primary carbon group, a secondary carbon group or a tertiary carbon group; and further provided that in $R^6$, when said second ring atom is bound to a halogen or a primary carbon group, none, one or two of the other ring atoms in $R^6$ and $R^7$ adjacent to said first ring atom are bound to a halogen or a primary carbon group, with the remainder of the ring atoms adjacent to said first ring atom being bound to a hydrogen atom; or in $R^6$, when said second ring atom is bound to a secondary carbon group, none, one or two of the other ring atoms in $R^6$ and $R^7$ adjacent to said first ring atom are bound to a halogen, a primary carbon group or a secondary carbon group, with the remainder of the ring atoms adjacent to said first ring atom being bound to a hydrogen atom; or in $R^6$, when said second ring atom is bound to a tertiary carbon group, none or one of the other ring atoms in $R^6$ and $R^7$ adjacent to said first ring atom are bound to a tertiary carbon group, with the remainder of the ring atoms adjacent to said first ring atom being bound to a hydrogen atom.

4. The process as recited in claim 3 wherein $R^6$ is

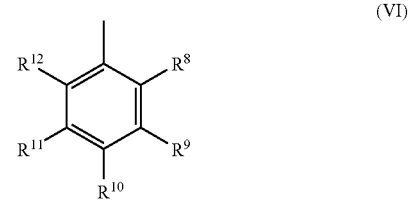

(VI)

and $R^7$ is

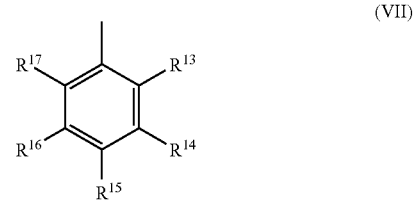

(VII)

wherein:
$R^8$ is a halogen, a primary carbon group, a secondary carbon group or a tertiary carbon group; and $R^9$, $R^{10}$, $R^{11}$, $R^{14}$, $R^{15}$, $R^{16}$ and $R^{17}$ are each independently hydrogen, hydrocarbyl, substituted hydrocarbyl or a functional group;

provided that:
when $R^8$ is a halogen or primary carbon group none, one or two of $R^{12}$, $R^{13}$ and $R^{17}$ are a halogen or a primary carbon group, with the remainder of $R^{12}$, $R^{13}$ and $R^{17}$ being hydrogen; or when $R^8$ is a secondary carbon group, none or one of $R^{12}$, $R^{13}$ and $R^{17}$ is a halogen, a primary carbon group or a secondary carbon group, with the remainder of $R^{12}$, $R^{13}$ and $R^{17}$ being hydrogen; or when $R^8$ is a tertiary carbon group, none or one of $R^{12}$, $R^{13}$ and $R^{17}$ is tertiary carbon group, with the remainder of $R^{12}$, $R^{13}$ and $R^{17}$ being hydrogen;

and further provided that any two of $R^8$, $R^9$, $R^{10}$, $R^{11}$, $R^{12}$, $R^{13}$, $R^{14}$, $R^{15}$, $R^{16}$ and $R^{17}$ vicinal to one another, taken together may form a ring.

5. The process as recited in claim 4 wherein:

if $R^8$ is a primary carbon group, $R^{13}$ is a primary carbon group, and $R^{12}$ and $R^{17}$ are hydrogen; or if $R^8$ is a secondary carbon group, $R^{13}$ is a primary carbon group or a secondary carbon group, and $R^{12}$ and $R^{17}$ are hydrogen; or if $R^8$ is a tertiary carbon group, $R^{13}$ is a tertiary carbon group, and $R^{12}$ and $R^{17}$ are hydrogen; or if $R^8$ is a halogen, $R^{13}$ is a halogen, and $R^{12}$ and $R^{17}$ are hydrogen.

6. The process as recited in claim 4 wherein:

$R^1$, $R^2$ and $R^3$ are hydrogen; and $R^4$ and $R^5$ are methyl; $R^{19}$, $R^{20}$, $R^{21}$, $R^{23}$ and $R^{24}$ are all hydrogen; $R^{22}$ is methyl; and $R^{18}$ methyl;

or $R^{19}$, $R^{20}$, $R^{21}$, $R^{23}$ and $R^{24}$ are all hydrogen; $R^{22}$ is ethyl; and $R^{18}$ ethyl; or $R^{19}$, $R^{20}$, $R^{21}$, $R^{23}$ and $R^{24}$ are all hydrogen; $R^{22}$ is isopropyl; and $R^{18}$ isopropyl; or $R^{19}$, $R^{20}$, $R^{21}$, $R^{23}$ and $R^{24}$ are all hydrogen; $R^{22}$ is n-propyl; and $R^{18}$ n-propyl; or $R^{19}$, $R^{20}$, $R^{21}$, $R^{23}$ and $R^{24}$ are all hydrogen; $R^{22}$ is chloro or bromo; and $R^{18}$ is a halogen.

7. The process as recited in claim 1 which is carried out at a temperature of about 70° C. to about 110° C.

8. The process as recited in claim 1 wherein there are about 3 to about 8 of said addition points.

9. The process as recited in claim 1, 2, 3, 4, 5, 6, 7, or 8 wherein ethylene is added at two or more second addition points to said process mixture.

10. The process as recited in claim 9 wherein said first addition points and said second addition points are the same.

* * * * *